United States Patent [19]
Klein et al.

[11] Patent Number: 5,625,121
[45] Date of Patent: Apr. 29, 1997

[54] MICE DEFICIENT IN NERVE GROWTH FACTOR RECEPTORS ENCODED BY TRKB

[75] Inventors: Rudiger Klein, Nussloch, Germany; Alexandra Joyner, Toronto, Canada; Mariano Barbacid, Lawrenceville, N.J.

[73] Assignee: Bristol-Myers Squibb Company, Princeton, N.J.

[21] Appl. No.: 114,859

[22] Filed: Oct. 14, 1993

[51] Int. Cl.$^6$ .................... C12N 5/00; C12N 15/00
[52] U.S. Cl. .................... 800/2; 435/325; 435/354; 935/60
[58] Field of Search ................ 800/2; 435/240.2; 935/60

[56] References Cited

FOREIGN PATENT DOCUMENTS

WO92/18149 10/1992 WIPO.

OTHER PUBLICATIONS

Lee et al (1992) Cell 69, 737–749.
Klein et al (1990) Cell 61, 647–656.
Cell, vol. 69, May 29, 1992, pp. 737–749, K.F. Lee et al., "Targeted Mutation of the Gene Encoding the Low Affinity NGF Receptor p75 Leads to Deficits in the Peripheral Sensory Nervous System".
J. Cell. Biochem., Supplement 17, part A, Jan. 9–31, 1993, p. 234, abstr. R. Klein et al. "Germline Targeting of the Mouse trkB Gene".
Nature, vol. 336, Nov. 24, 1988, pp. 348–352, S.L. Mansour et al. "Disruption of the Proto–oncogene int–2 in Mouse Embryo–derived Stem Cells: A General Strategy For Targeting Mutations to Non–selectable Genes".
Cell, vol. 75, No. 1, Oct. 8, 1993, pp. 113–122, R. Klein et al. "Targeted Disruption of the trkB Neurotrophin Receptor Gene Results in Nervous System Lesions and Neonatal Death".

Trends in Genetics, 5 (3), pp. 70–76, 1989.

T.M. DeChiara et al., Nature, 345, pp. 78–80, 1990.

S.L. Knight et al., Nucleic Acids Research, 8, 24, pp. 5949–5964, 1990.

P.L. Schwartzberg et al., Science, 246, pp. 799–803, 1989.

O. Smithies, et al., Nature, 317, pp. 230–234, 1985.

*Primary Examiner*—Deborah Crouch
*Attorney, Agent, or Firm*—Timothy J. Gaul

[57] ABSTRACT

The present invention provides mice and mouse cell lines having a homozygous or heterozygous deficiency in a gene encoding a neurotrophin receptor. In a preferred embodiment of this invention, mice and cell lines carry a trkB locus specifically targeted within its tyrosine protein kinase sequences. Mice homozygous for this mutation express $gp95^{trkB}$ receptor of unknown function but not the high affinity functional $gp145^{trkB}$ tyrosine protein kinase receptors. This mutation results in multiple CNS and PNS neuronal deficiencies and in a postembryonic lethal phenotype. Such genetically modified mice are useful in model systems for studying human diseases involving neuronal degeneration and neuronal cell loss, as well as in screening for genes, proteins, or other compounds that may prevent or impede neuronal cell death or stimulate neuronal regeneration.

3 Claims, 9 Drawing Sheets

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
CCTTGCGGCC GCTCTTCAGA ATTTATTAAA GAG                                           33
```

(2) INFORMATION FOR SEQ ID NO:2:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

```
GTCGCCCTCG AGACAGACAC CGTAGAACTT G                                             31
```

(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
GCTGGACACT GGGACTGCCA GGCC                                                     24
```

(2) INFORMATION FOR SEQ ID NO:4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

```
CTACCCGGTA GAATTCCTCG AG                                                       22
```

MICE DEFICIENT IN NERVE GROWTH FACTOR RECEPTORS ENCODED BY TRKB

FIELD OF THE INVENTION

The present invention relates to the fields of neurology and genetically altered mice. Specifically, the present invention relates to mice that are deficient in the normal expression of one or more wild-type genes, to mice heterozygous for such a deficiency, and to cell lines that am homozygous or heterozygous for this deficiency.

BACKGROUND OF THE INVENTION

The functional receptors responsible for mediating the trophic properties of the nerve growth factor (NGF) family of neurotrophins have been recently identified as members of the trk family of tyrosine protein kinases (Barbacid, 1993). Neurotrophins are growth factors responsible for development and maintenance of neurons. These molecules exert their biological effect through high affinity signaling receptors located on the surface of specific types of neurons.

To date, three different loci, designated trk, trkB and trkC, have been identified. See U.S. Ser. No. 837,814, filed Feb. 25, 1992, which is incorporated herein by reference. The product of the trk proto-oncogene, a 140 kDa cell surface tyrosine protein kinase designated as gp140trk (Martin-Zanca etal., 1989), is the high affinity receptor for NGF (Kaplan et al., 1991; Klein et al., 1991a). The related $gp145^{trkB}$ tyrosine protein kinase (Klein et al., 1989) serves as the signaling receptor for two related neurotrophins, brain-derived neurotrophic factor (BDNF) (Klein et al., 1991b; Soppet etal., 1991; Squinto et al., 1991) and neurotrophin-4 (NT-4) (Berkemeier et al., 1991, Klein et al., 1992; Ip etal., 1992). Finally, $gp145^{trkC}$, a tyrosine protein kinase encoded by the third member of this gene family, trkC, appears to be primarily responsible for mediating the trophic properties of neurotrophin-3 (NT-3) (Lamballe et al., 1991). This gene may also code for additional tyrosine protein kinase isoforms that differ from $gp145^{trkC}$ by the presence of a small number of amino acid residues within their respective catalytic kinase domains (Lamballe et al., submitted for publication).

The trkB gene is a large (>100 kbp) and complex locus capable of directing the synthesis of multiple transcripts (Klein et al., 1989; 1990a; Middlemas et al., 1991). Some of these transcripts direct the synthesis of the $gp145^{trkB}$ tyrosine protein kinase receptor. Other transcripts however, code for a second class of trkB receptors that lack a catalytic kinase domain. One of these receptors, $gp95^{trkB}$, is abundantly expressed in adult mouse brain (Klein etal., 1990a). Nucleotide sequence analysis of cDNA clones corresponding to these transcripts predicts that $gp95^{trkB}$ has the same extracellular and transmembrane domains as $gp145^{trkB}$, but contains a very short cytoplasmic region of 23 amino acid residues of which the last eleven bear no resemblance to any of the sequences present in $gp145^{trkB}$ (Klein et al., 1990a). Molecular analysis of rat trkB cDNA clones has identified a second non-catalytic trkB receptor isoform with a predicted sequence identical to that of $gp95^{trkB}$ except for the presence of a unique nine amino acid-long sequence at its carboxyl terminus (Middlemas et al., 1991).

In situ hybridization analysis has shown that the trkB gene is widely expressed in multiple structures of the central and peripheral nervous systems (Klein et al., 1989; 1990a, b). In the CNS, trkB transcripts have been observed in the cerebral cortex, hippocampus, thalamus, choroid plexus, granular layer of the cerebellum, brain stem and spinal cord. In the PNS, trkB expression is observed in many cranial ganglia including the trigeminal, facial, acoustic, IX/X superior and IX/X inferior ganglia, the retina and ophthalmic nerve, the vestibular system, multiple facial structures, the submaxillary glands and dorsal root ganglia. Analysis of trkB transcripts with probes specific for the catalytic and non-catalytic trkB receptors revealed a rather distinct pattern of expression. For instance, in the adult mouse brain, $gp145^{trkB}$ transcripts have been detected in the cerebral cortex, thalamus and the pyramidal cell layer of the hippocampus. In contrast, transcripts encoding the non catalytic $gp95^{trkB}$ receptor appear to be most prominent in structures containing non-neuronal cells such as the ependymal cell layer of the ventricles and the choroid plexus (Klein et al., 1990a).

SUMMARY OF THE INVENTION

The present invention provides mice and mouse cell lines that carry disrupted genes for each of the trk family of neurotrophin receptor genes. This disruption, achieved by homologous recombination, completely abolishes expression of the corresponding high affinity signaling neurotrophin receptor. Specifically, the present invention describes mice wherein the trkB locus has been modified so as to be deficient in expression of the wild-type trkB gene product. In a preferred embodiment of this invention, mice carry a trkB locus specifically targeted within its tyrosine protein kinase sequences. Mice homozygous for this mutation express the non-catalytic $gp95^{trkB}$ receptor of unknown function but not the high affinity functional $gp145^{trkB}$ tyrosine protein kinase receptors. This mutation results in multiple CNS and PNS neuronal deficiencies and in a postembryonic lethal phenotype.

Also in accordance with the present invention are mice and mouse cell lines heterozygous for the same trkB deficiency. Such genetically modified mice are useful in model systems for studying human diseases involving neuronal degeneration and neuronai cell loss, as well as in screening for genes, proteins, or other compounds that may prevent or impede neuronal cell death or stimulate neuronal regeneration.

Figure 1A:
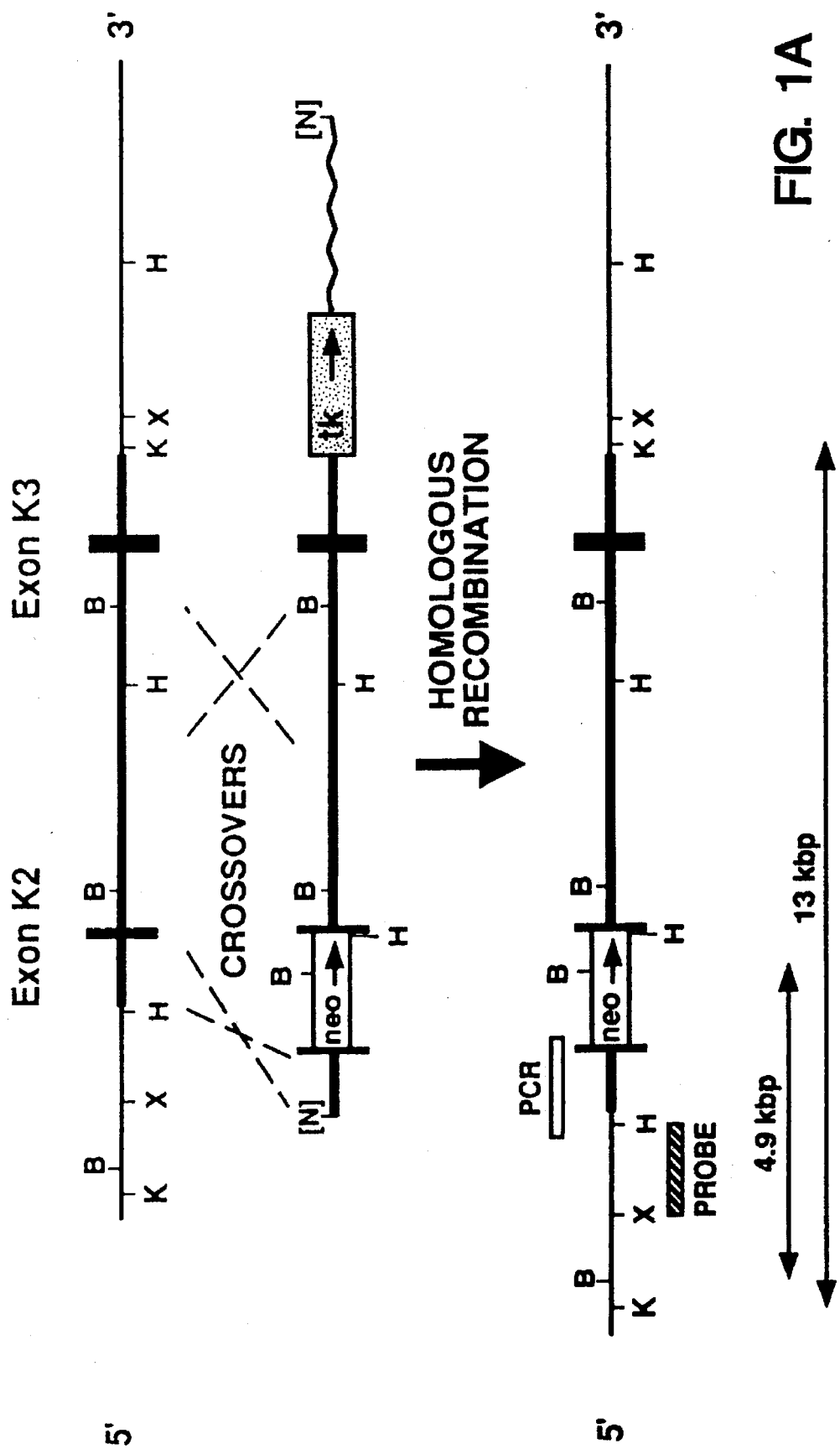
FIG. 1(A–C) Targeting of the tyrosine protein kinase domain of the mouse TrkB gene in D3 ES cells.

1(A). Schematic diagram of the strategy utilized to target the trkB locus. Vertical black boxes represent the second (K2) and third (K3) exons of the trkB tyrosine kinase domain. Thick horizontal lines represent trkB genomic sequences incorporated into the targeting vector pFRK90. Thin horizontal lines represent additional trkB genomic sequences. Putative cross-overs between the endogenous trkB locus and the targeting pFRK90 DNA are indicated as crossed stippled lines. The PGK-1/Deo cassette is indicated by an open box labeled as "neo". The HSVTK cassette is indicated by a shaded box labeled as "tk". The arrows inside both boxes indicate the direction of transcription. The wavy line represent bacterial plasmid sequences. Cleavage sites for restriction endonucleases BamHI (B), HindIII (H), KpnI (K), and XhoI (X) are indicated. The NotI cleavage site used to lineadze pFRK90 DNA is indicated in brackets. The region amplified by PCR to identify $G418^R/Ganc^R$ ES cell clones carrying homologous recombination events is indicated by a small open box. The 1.4 kbp XhoI-HindIII DNA probe use to identify the diagnostic 4.9 kbp BamHI and 13 kbp KpnI DNA fragments (indicated by arrows) is indicated by a small hatched box.

1 (B). Southern blot analysis of PCR-positive G418$^R$/Ganc$^R$ ES cell clones. Genomic DNA extracted from representative PCR-positive G418$^R$/Ganc$^R$ ES cell clones (lanes 1 to 4) or untransfected D3 ES cells (lane 5) were digested with BamHI or KpnI as indicated as submitted to Southern blot analysis using the probe indicated in (A). The wild type trkB allele generates 4.1 kbp BamHI and 11.0 kbp KpnI fragments, whereas the targeted allele yields the diagnostic 4.9 kbp BamHI and 13.0 kbp KpnI fragments indicated in (A).

1 (C). Southern blot analysis of a representative litter derived from crossing trkB$^{TK}$ (±) mice. The wild type allele trkB produces a 4.1 kbp BamHI fragment whereas the targeted allele produces a 4.9 kbp BamHI fragment. Half-filled symbols represent heterozygous (±) genotypes at the trkB locus. Filled symbols indicate animals that died. Sexes of the offspring were not determined and are shown as diamonds.

FIG. 2(A–B) Expression of trkB receptors in trkB$^{TK}$ mutant mice. Heads (A) and brains (B) were isolated from either newborn (P0) trkB$^{TK}$ (+/+), (±), (–/–) mice or adult (Ad) mice and submitted to Western blot analysis for the expression of the (A) gp145$^{trkB}$ tyrosine protein kinase and the (B) non-catalytic gp95$^{trkB}$ receptors. Samples were incubated with either (a) an unrelated mouse monoclonal antibody; (b) mouse anti-gp145$^{trkB}$ monoclonal antibody 18–29.2; (c) rabbit preimmune or (d) immune polyclonal antiserum #104 raised against a peptide corresponding to the 13 carboxy-terminal amino acid residues of the non-catalytic gp95$^{trkB}$ protein (Klein et al., 1990a). Immunoprecipitates were electrophoresed in 7.5% SDS-PAGE, blotted onto nitrocellulose membranes and incubated with either (A) a rabbit polyclonal antiserum raised against a peptide corresponding to the 14 carboxy-terminal amino acids of the trk tyrosine protein kinase receptor that also recognizes gp145trkB (#42) or (B) antiserum #104. The migration of gp145$^{trkB}$ and gp95$^{trkB}$ receptors is indicated by arrows. Molecular weight markers include myosin (200,000), phosphorylase B (97,000), and albumin (69,000).

FIG. 3 (A–D) Abnormalities in regions of the central and peripheral nervous systems of trkB$^{TK}$ (–/–) mice. (A,B) Trigeminal ganglion; (C,D) Facial motor nucleus. Scale bar (A–D) is 50 μm.

3 (A). Coronal section through the trigeminal ganglion of a wild type (+/+) mouse, 375 μm from its antedor origin.

3(B). Coronal section through the trigeminal ganglion of a trkB$^{TK}$ (–/–) mouse, 375 μm from its anterior origin.

3(G). Coronal section through the center of the brainstem FMN of a wild type (+/+) mouse. The FMN consists of a group of large motor neurons coalesced into several subnuclei (dashed lines), surrounded by an area of reduced cellular density (small arrows in C).

3 (D). Coronal section through the center of the brainstem FMN of a trkB$^{TK}$ (–/–) mouse. The FMN of the trkB$^{TK}$ (–/–) animals has a decreased cellular density of otherwise morphologically indistinguishable motor neurons.

FIG. 4(A–B) Number of neurons in the trigeminal ganglion and facial motor neurons of trkB$^{TK}$ (+/+) and (–/–) mice.

4 (A). Graphic representation of the number of neurons ±SEM in sedal sections of the trigeminal ganglion of trkB$^{TK}$ (+/+) and (–/–) mice. T-test comparisons between the number of ganglion cells in the trkB$^{TK}$ (–/–) and (+/+) mice reveals a statistically significant loss of ganglion cells (p <.001).

4 (B). Graphic representation of neuron number ±SEM in serial sections of the facial motor nucleus of trkB$^{TK}$ (+/+) and (–/–) mice. The FMN of the trkB$^{TK}$ (–/–) mice is reduced in both cell number (p<.002) and total area compared to the corresponding structure of its (+/+) and (+/–) litter mates.

FIG. 5(A–D) Abnormalities in regions of the nervous systems of trkB$^{TK}$(–/–) mice. (A, B) Dorsal root ganglion; (C, D) Lumbar motor neurons. Scale bar (A, B) is 100 μm; (C, D), 50 μm.

5 (A). Coronal section through the center of a dorsal root ganglion (DRG) of a wild type (+/+) mouse.

5 (B). Coronal section through the center of a DRG of a trkB$^{TK}$(–/–) mouse.

5 (C) Coronal section through Rexed layers 8 (VIII) and 9 (IX) of the lumbar spinal cord of a wild type (+/+) mouse. Motor neurons are seen as large cells with a dark staining cytoplasm and pale nucleus (arrows).

5 (D). Coronal section through a similar region of the spinal cord of a trkB$^{TK}$(–/–) mouse. Although the gross morphology of the spinal cord and differentiation of Rexed layers 8 and 9 do not appear different from normal litter mates, there is a reduced density of motor neurons in the trkB$^{TK}$(–/–) mouse.

Figure 6A:
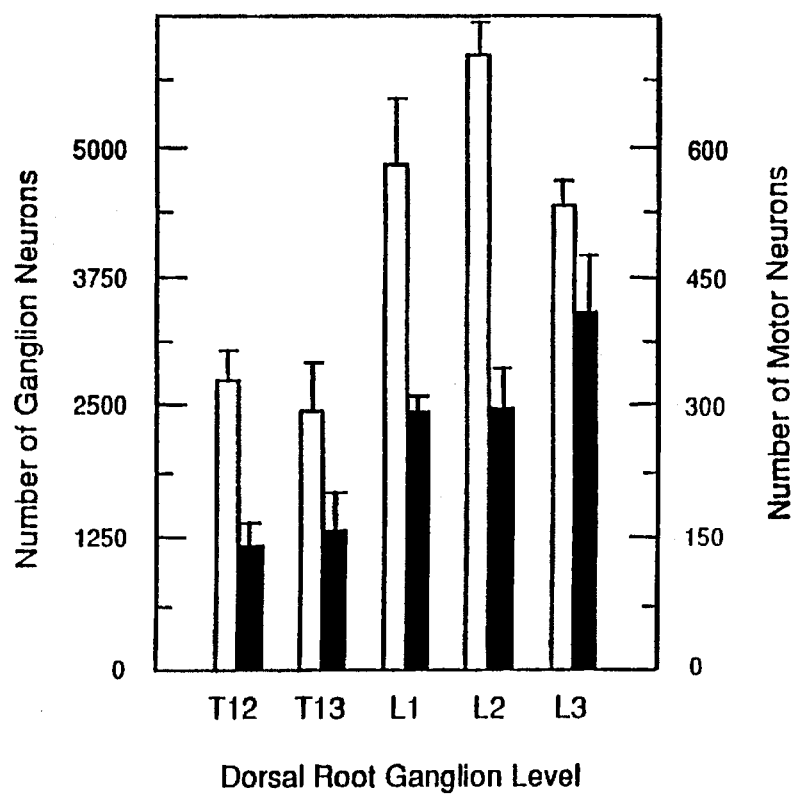
Figure 6B:
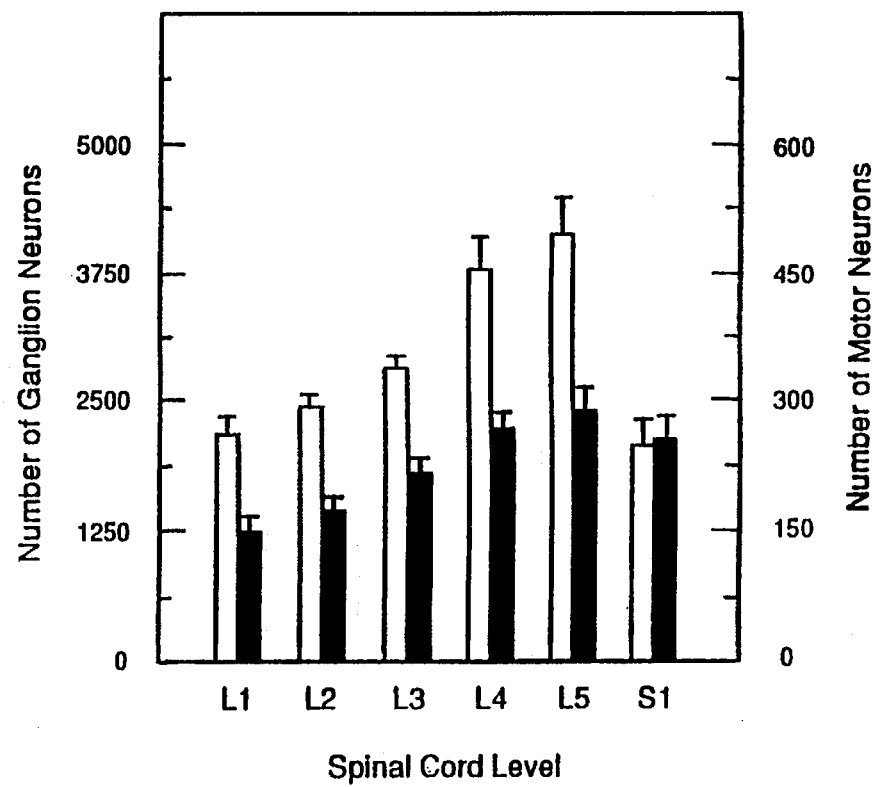

FIG. 6(A–B) Number of neurons in the DRGs and lumbar spinal cord of trkB$^{TK}$ (+/+) and (–/–) mice.

6(A). Graphic representation of ganglion cell number ±SEM in the DRGs from spinal cord thoracic levels 12 through lumbar levels 3 (T12-L3) of trkB$^{TK}$ (+/+) and (–/–) mice. Ganglion cell numbers in the trkB$^{TK}$ (–/–) animals compared to (+/+) mice are significantly reduced (p<.05) at all spinal cord levels by approximately 30–50%.

6(B). Graphic representation of the number of motor neurons ±SEM in Rexed layers 8 and 9 in the ventral spinal cord from lumbar level 1 through sacral level 1 (L1-S1) of trkB$^{TK}$ (+/+) and (–/–) mice. Motor neurons in the trkB$^{TK}$ (–/–) L1-L5 spinal cord am reduced by approximately 35% (p<.01) as compared to the corresponding neurons of (+/+) and (±) mice.

DETAILED DESCRIPTION OF THE INVENTION

Definition of Terms

The terms used in this specification are defined as follows. These definitions apply to these terms as used throughout this specification, unless otherwise limited in specific instances.

The terms "deficient" or "deficiency" as used with respect to a gene refers to an allele altered (e.g., by homologous recombination, resulting in the insertion of foreign sequences) such that either no product or only an inoperative fragment of the wild type product can be expressed. A "deficient" allele within this definition may also comprise a gene deletion, wherein the gene has been deleted in toto; a gene disruption, wherein the gene is interrupted by another gene or nucleic acid sequence; a partial deletion, wherein one or more nucleic acid sequences or deleted; a substitution, wherein one or more bases are replaced by other bases; and other such mutations as will be understood by persons having ordinary skill in the art. Such deletions, disruptions, and substitutions may take place in, for example, the coding region, a promoter, or an enhancer.

The term "homozygous" as used with respect to a gene deficiency refers to a genome having deficient alleles at corresponding loci on homologous chromosomes.

The term "heterozygous" as used with respect to a gene deficiency refers to a genome having a deficient allele at the corresponding locus on one homologous chromosome.

Process of preparation

Mice heterozygous or homozygous for the desired gene deficiency are prepared using the principles of homologous recombination. Homologous recombination has long been known in prokaryotic species (for a review, see *Trends in Genetics* (1989)). Its use in mice was pioneered by the work of Smithies and Capecchi. See Smithies, O. et al. (1985), Schwartzberg, P. L., et al., (1989), DeChiara, T. M., et al., (1990). Based on homologous recombination principles, mice homozygous or heterozygous for the desired deficient gene may be constructed by the following steps:

(1) isolating the wild-type locus (or part of it) for the target gene (e.g., using a cDNA probe on a genomic library), (2) modifying or disabling the identified locus by genetic engineering techniques (e.g., by gene disruption), (3) preparing suitable host cells (e.g., male ES cells) capable of accepting exogenous DNA, (4) introducing the deficient gene into the prepared host cells (e.g., by electroporation with a replacement vector), (5) selecting cells incorporating the deficient gene, preferably by a process involving homologous recombination, (6) injecting the identified cells into early-stage mouse embryos or blastocysts, (7) identifying chimeric animals (usually male) made from the ES cells, (8) crossing the chimeras with tester animals, (9) identifying offspring heterozygous for the desired gene deficiency (usually based on coat color),

(10) crossing heterozygous mice, and

(11) identifying offspring homozygous for the desired gene deficiency.

The wild-type gene and DNA fragments containing all or part of its genomic sequences may be identified by screening a mouse genomic library (e.g., from 129 Sv mice) with a probe having part of the sequence of the desired gene. Upon identification, the target wild-type gene may be modified by conventional genetic engineering techniques, making it "deficient" as defined above. One particularly useful method of modifying the target gene is disruption by a marker gene, which will aid in selection of cells that have successfully undergone homologous recombination (see below).

Particularly suitable host cells for the process of homologous recombination needed to mutate the desired gene are male embryonic stem cells. These cells can be successfully cultured for a large number of generations under conditions in which they will not differentiate, thus releasing their ability to contribute to all lineages, which is an absolute requirement to generate a mouse carrying the mutations introduced in these cells.

The deficient gene is then introduced into the host cells in a suitable manner, such as electroporation. Once taken up by the host cells, homologous recombination with the corresponding endogenous gene may occur.

To select cells in which the desired homologous recombination event has taken place, a marker may be used. Suitable markers include genes conferring resistance to such antibiotics as neomycin. For example, a bacterial neo gene confers resistance to neomycin and such analogues as G418. The marker gene may be inserted in the target wild-type gene, thereby disabling the target gene while providing a selectable marker for cells having taken up. Among the cells that survive treatment with neomycin or one of its analogues (i.e., cells that are Neo$^+$), a limited fraction will have replaced the wild-type gene with the desired deficient gene.

The deficient gene may, however, enter the host genome by random insertion instead of homologous recombination. Such nonhomologous recombinants will be Neo$^+$ without the desired replacement of the wild-type gene. Therefore, to further select homologous recombinants, the ends of the deficient gene may have such negative markers as the herpes simplex virus thymidine kinase (HSVTK) gene. The HSVTK gene product converts gancyclovir into a toxic metabolite. In a homologous recombination event, however, the HSVTK gene will not be present. Therefore, desired recombinants will be resistant to gancyclovir and may be further selected by gancyclovir treatment.

After biological resolution, still most recombinational events will be of the non-homologous type (in some cases, as many as 99% will be non-homologous recombinational events). To identify the true homologous recombinants, molecular screening is necessary either by Southern blot or PCR. This technology has been previously described (Joyner et al., 1989).

When a suitable ES cell clone has been identified, the host cells may be injected into early-stage embryos or blastocysts, and reintroduced into a pseudopregnant female. Chimedc animals will generally result from at least some of these embryos, their tissues deriving in part from the selected clone. In some of these chimeras, the ES cell clone carrying the targeted gene will contribute to the germ line. If so, the next generation of animals will be entirely derived from the ES cell clone selected in vitro after homologous recombination as described above.

The heterozygous progeny can be cross-bred to yield homozygous animals. Confirmation of the allelic structure of the mice can be ascertained, for example, by PCR and Southern blotting.

DETAILED DESCRIPTION OF PREFERRED EMBODIMENTS

Using recombinant DNA technology, a targeting vector carrying an altered trkB genomic sequence was constructed. This vector was used to destroy the endogenous trkB locus of ES cells by a process involving electroporation of the vector DNA followed by homologous recombination with endogenous trkB sequences.

The preferred mutation eliminates expression of gp145$^{trkB}$, the signaling receptor for BDNF and NT-4, without eliminating expression of the non-catalytic isoform, gp95$^{TrkB}$. Mice homozygous for this mutation, trkB$^{TK}$ (−/−), develop to birth. However, these animals do not display any signs of feeding activity and most die at P1. Neuroanatomical examination of these mice revealed significant neuronai deficiencies in the central (facial motor nucleus and spinal cord) and peripheral (trigeminal and dorsal root ganglia) nervous systems. However, qualitative examination of other neural structures (cerebral cortex, hippocampus) known to express trkB$^{TK}$ transcripts do not appear to be affected, perhaps due to compensatory mechanisms. These findings illustrate the critical role of the gp145$^{trkB}$ tyrosine protein kinase receptor in the mammalian nervous system.

Targeting the Mouse trkB Locus: Experimental Approach

A mouse genomic library derived from NIH3T3 cells was screened with a 2.7 kbp SalI trkB cDNA probe encompassing sequences encoding the transmembrane and cytoplasmic domains of gp145$^{trkB}$. One of the library phage was found to contain a 21 kbp insert which included the second and third exons of the tyrosine protein kinase region of trkB separated by a 6 kbp long intron (FIG. 1). Since the exon/intron structure of the trkB locus has not been fully established, we will refer to these exons as K2 and K3. Exon K2 is 173 bp long (nucleotides 2225 to 2397 of pFRK43; see Klein et al., 1989) and contains domains III through V of the tyrosine protein kinase region (Hanks et al., 1988). Exon K3 is 235 bp long (nucleotides 2398 to 2632 in pFRK43) and contains domains VI and VII.

Figure 1B:
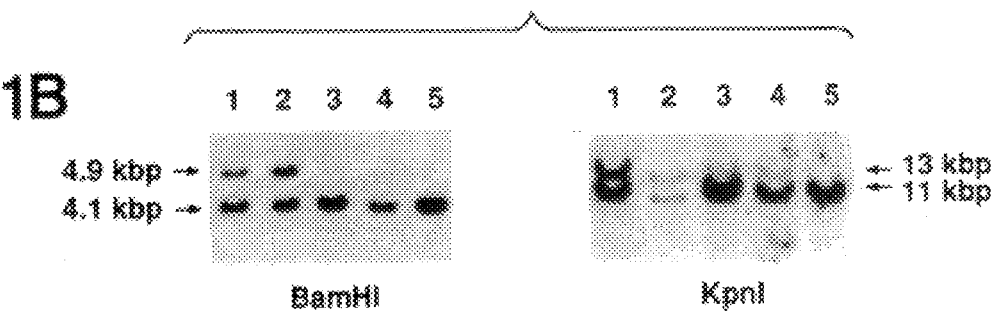

These genomic sequences were used to construct the replacement vector, pFRK90, by replacing 33 bp of exon K2 (nucleotides 2330 to 2362 of pFRK43) with a PGK-1/neo cassette (McBurney et al., 1991)inserted in the same transcriptional orientation as the trkB gene (FIG. 1 ). The short arm of pFRK90 was generated by PCR-aided amplification of phage genomic sequences and consists of 104 bp of exon K2 and 750 bp of upstream intronic sequences. The 7.250 bp long arm of pFRK90 was located 3' to the PGK/neo cassette and contains the remaining sequences of exon K2, the 6 kbp long K2/K3 intron, exon K3 and 1 kbp of downstream intronic sequences (FIG. 1 ). A thymidine kinase cassette, used for negative selection of cells carrying non-homologous recombination (Mansour etal., 1988), was inserted 3' of the genomic trkB sequences.

pFRK90 DNA was linearized with NotI and electroplated into $5 \times 10^7$ D3 ES cells (D3 clone) as described in Example 1 hereinafter. Two days later, the electroplated cells were placed under dual selection in the presence of G418 and gancyclovir. This double selection protocol resulted in a 10-fold enrichment over G418 selection alone. A total of 800 $G418^R/Ganc^R$ double resistant D3 ES cell clones were picked and screened by PCR as described (Joyner et al., 1989). Nine ES cell clones found to be positive in the initial PCR screen were subsequently submitted to Southern blot analysis. As illustrated in FIG. 1B, a probe derived from intronic sequences located upstream of pFRK90 detected a 4.9 kbp BamHI (4.1 kbp in wild type trkB DNA) and a 13 kbp KpnI (11 kbp in wild type trkB DNA) DNA fragment diagnostic of homologous recombinational events in eight out of nine PCR positive ES cell clones. These results indicate that the targeting frequency was one clone in 90 $G418^R/Ganc^R$ double-resistant ES cells.

Generation of trkB Mutant Mice

Targeted ES cell clones were injected into C57Bl/6J blastocysts and transferred into the uteri of pseudopregnant CD1 recipient mothers (see Example 1 hereinafter). Of a total of five clones injected, three of them (K2-19A, K2-24 and K2-29) generated chimeric offspring with ES cell contributions ranging from 20 to 90 % as judged by the proportion of agouti coat color. Three chimeric males derived from the K2-29 clone exhibited greater than 50% agouti coat color. These chimeras were bred to C57Bl/6J mice (as well as to 129Sv mice) and found to transmit the targeted allele through the germ line. Breeding of two chimeric siblings derived from an independent ES cell clone (K2-19A) which displayed weak to moderate (20% to 40%) proportion of agouti coat color also resulted in germ line transmission of the targeted trkB gene. Unless otherwise stated, the results described in this study were obtained with mice derived from the K2-29 ES cell clone.

Figure 1C:
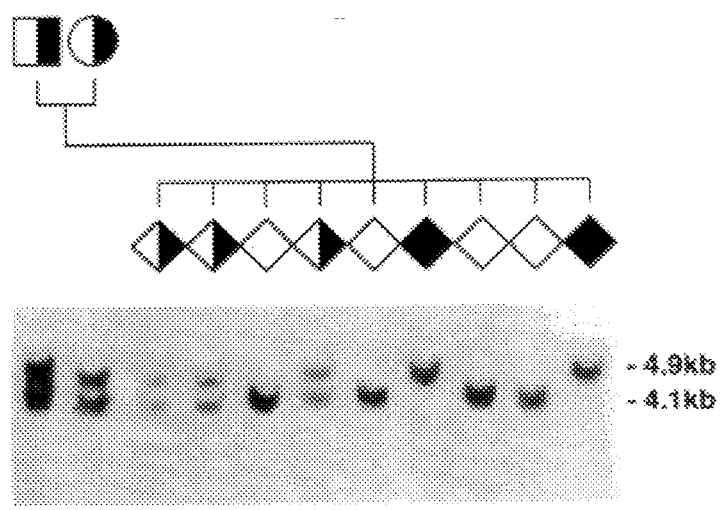

Genotyping of the agouti offspring produced the expected frequency of 50% heterozygotes. These mice, from now on designated as trkB$^{TK}$ (±), grew normally and showed no obvious anatomical or behavioral defects. To study the phenotypic consequences of elimination of a functional trkB tyrosine protein kinase, we crossed these trkB$^{TK}$ (±) heterozygous animals. The resulting litters were normal in size and all the animals appeared normal at the time of birth. Genotypic analysis of tail biopsies from 116 offspring mice showed that homozygous trkB$^{TK}$ (−/−) animals were born at a frequency of 23.3% indicating that mice lacking gp145$^{trkB}$ receptors can develop to birth (Table 1). FIG. 1C depicts a Southern blot analysis of a representative litter.

TABLE 1

| Genotypic analysis of the offspring of trkB$^{TK}$ (+/−) heterozygous mice | | |
|---|---|---|
| GENOTYPE | NUMBER OF MICE | PERCENTAGE |
| (+/+) | 33 | 28.4% |
| (+/−) | 56 | 48.3% |
| (−/−) | 27 | 23.3% |

Expression of trkB Receptors

Figure 2A:
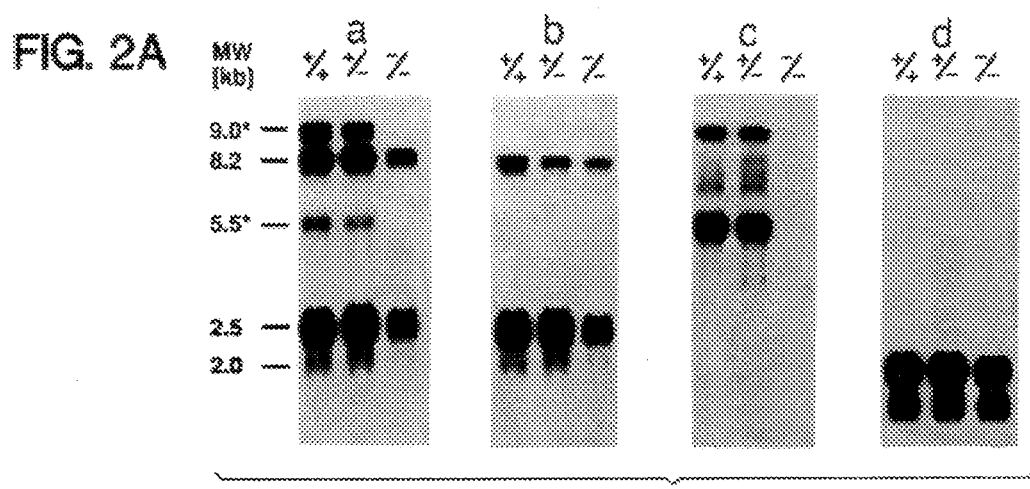

To verify that the targeted trkB$^{TK}$ (−/−) animals did not express the catalytic gp145$^{trkB}$ receptor, we immunoprecipitated protein lysates obtained from heads of newborn wild-type (+/+), trkB$^{TK}$ (±) and trkB$^{TK}$ (−/−) animals with a monoclonal antibody elicited against the tyrosine protein kinase domain of gp145$^{trkB}$. The resulting immunoprecipitates were submitted to Western blot analysis using pan anti-trk antibodies. As shown in FIG. 2A, the homozygous trkB$^{TK}$ (−/−) animals did not show detectable gp145$^{trkB}$ protein whereas the trkB$^{TK}$ (±) heterozygous displayed reduced levels of this receptor. Similar results were obtained in parallel experiments in which the protein lysates were immunoprecipitated with another trkB specific antiserum raised against a peptide corresponding to amino acids 794–808 of the trkB receptor (Klein et al., 1989).

Figure 2B:
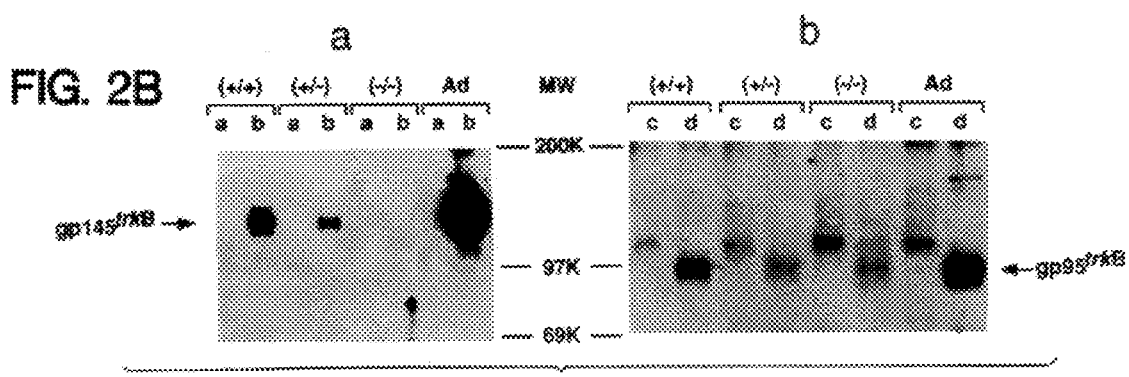

Targeting of trkB genomic sequences encoding the tyrosine protein kinase domain of gp145$^{trkB}$ should not disrupt expression of the non-catalytic gp95$^{trkB}$ receptor (Klein et al., 1990a). To confirm that the phenotypic properties (see below) of the targeted trkB$^{TK}$ (−/−) mice were due exclusively to the elimination of the gp145$^{trkB}$ tyrosine protein kinase receptors we tested for the presence of gp95$^{trkB}$ in these animals. As shown in FIG. 2B, the homozygous trkB$^{TK}$ (−/−) mice retained the ability to express the non-catalytic gp95$^{trkB}$ receptors at levels comparable to those of their heterozygous litter mates.

Phenotypic Analysis of trkB$^{TK}$ (−/−) Mice

As indicated above, all offspring derived from crosses of heterozygous trkB$^{TK}$ (±) mice appeared normal within a few hours after birth. The first symptomatic difference could be observed at approximately twelve hours when some of the newborn animals were found to be without milk in their stomachs. Most of these animals died by P1, although some survived as long as P3. Subsequent Southern blot analysis of tail biopsies established that these mice were homozygous for the trkB$^{TK}$ mutation.

Gross examination of these trkB$^{TK}$ (−/−) animals at the day of birth revealed that they were the same size (crown-rump) as their unaffected litter mates and did not exhibit any apparent physical deformities. Since these trkB$^{TK}$ (−/−) animals did not take nourishment, they were checked for abnormalities in their digestive system. No gross lesions were observed in the head, including cleft lip or palate, although in a few instances there appeared to be a slight macroglossia. The esophagus appeared normal and without stricture, as did the stomach and pyiorus. One difference observed in the trkB$^{TK}$ (−/−) mice compared to their (+/+) and (±) litter mates was the occasional occurrence of a gas-expanded stomach, most likely due to an absence of maternal milk.

A rudimentary neurological exam was performed on these newborn mice to try to identify gross behavioral differences between the trkB$^{TK}$ (+/+), (±) and (−/−) animals. We found that upon a light stroking under the chin, the (+/+) and (±) animals responded by orienting to the side of the stimulus. These animals also responded by opening and closing their mouths in what might be interpreted to be a sucking pattern. This behavioral pattern was not observed in the trkB$^{TK}$ (−/−) mice. These animals did not orient towards the stimulus and for the most part never opened their mouth except for an occasional gasp. Subjectively, it appeared that the trkB$^{TK}$ (+/+) and (±) animals had a greater number of vocalizations. All other parameters of behavior appeared normal. For example, all of the mice examined wriggled in response to being handled. Homozygous trkB$^{TK}$ mice derived from the K2-19A ES cell line also exhibited the same phenotype.

It was not clear whether the lack of milk in the stomachs of the trkB$^{TK}$ (−/−) mice was due to the mother refusing to feed them, or to an intrinsic defect in these animals. To address this question, manual feeding the trkB$^{TK}$ (−/−) newborns was attempted with milk formula through a syringe attached to a small caliber tube inserted into their mouths. While this procedure was successful with the (+/+) and (±) mice, the trkB$^{TK}$ (−/−) animals inhaled instead of swallowed the milk.

The trkB$^{TK}$ (−/−) mice did not develop properly after birth, showing clear signs of cachexia and retarded development by P2, presumably due to their inability to properly feed themselves. As indicated above, most of the trkB$^{TK}$ (−/−) mice died at P1. Those that occasionally survived were found to be severely cachectic and died of marasmus. To avoid the possibility that the observed anatomical abnormalities might have been due to wasting, animals were exclusively analyzed at P0.

trkB$^{TK}$ (−/−) Mice Have Lesions in the Neuronal Systems Involved in Feeding

Figure 3A:
Figure 3B:
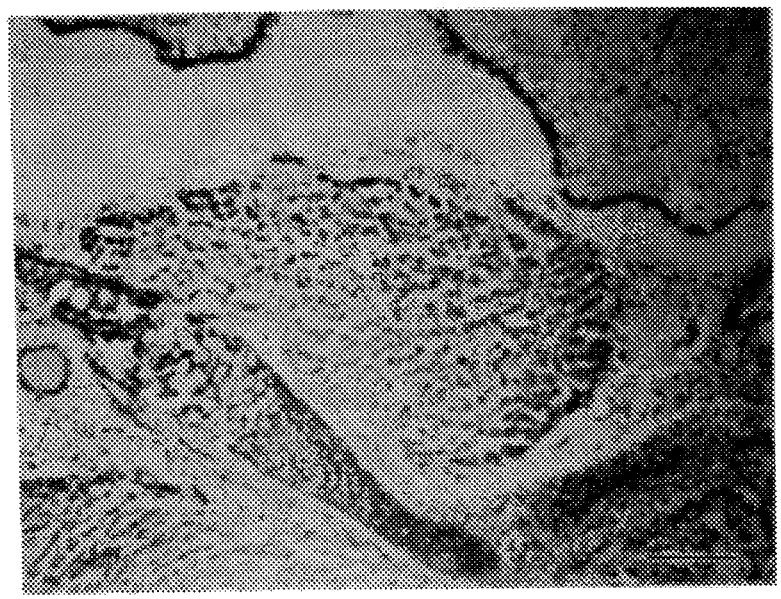
Figure 4A:
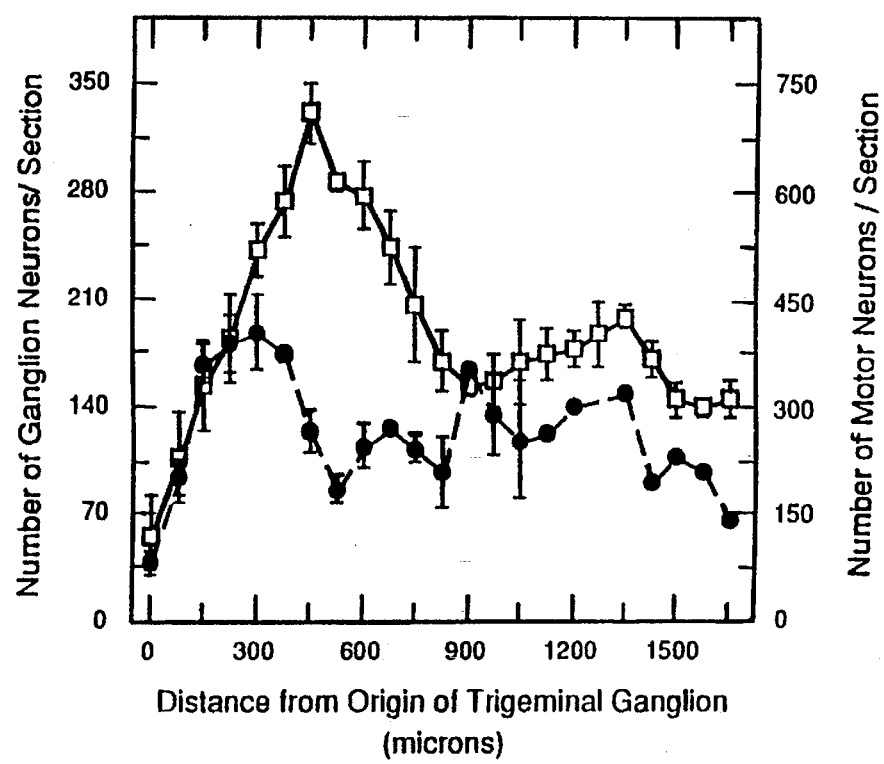

Feeding behavior in mammals is controlled by complex interactions among several neuronal pathways. The sensory system, for the most part, is subserved by the maxillary and mandibular branches of the trigeminal nerve. The motor system is controlled by branches of the facial nerve with contributions from the mandibular branch of the trigeminal nerve (Walton, 1977). To determine whether there was any physical deficit which would underlie the observed behavioral abnormalities, we examined the sensory ganglion of the trigeminal nerve and the motor nucleus of the facial nerve of these trkB$^{TK}$ (−/−) mice. Both of these structures have been previously shown to express trkB transcripts during development (Klein etal., 1989). Upon gross examination, the trigeminal ganglion of the trkB$^{TK}$ (−/−) mice appeared smaller than those of the normal litter mates (FIG. 3A, B). Microscopic examination revealed a significant (p<0.001) reduction in the number of ganglion cells present in the trkB$^{TK}$ (−/−) mice (8,469±698; n=4) compared to the (+/+) (21,132±567; n=4) and (±) (20,314±927; n=3) animals. The number of ganglion cells found in the (+/+) animals compares well with that reported in a previous study (Davies and Lumsden, 1984). The largest difference in ganglion cell number between the trkB$^{TK}$ (−/−) and (+/+) mice was observed in the anterior one-half of the ganglion (FIG. 4A). However, there was no detectable difference in the size of the ganglion cells of the trkB$^{TK}$ (−/−) mice when compared to the (+/+) or (±) animals.

Figure 3C:
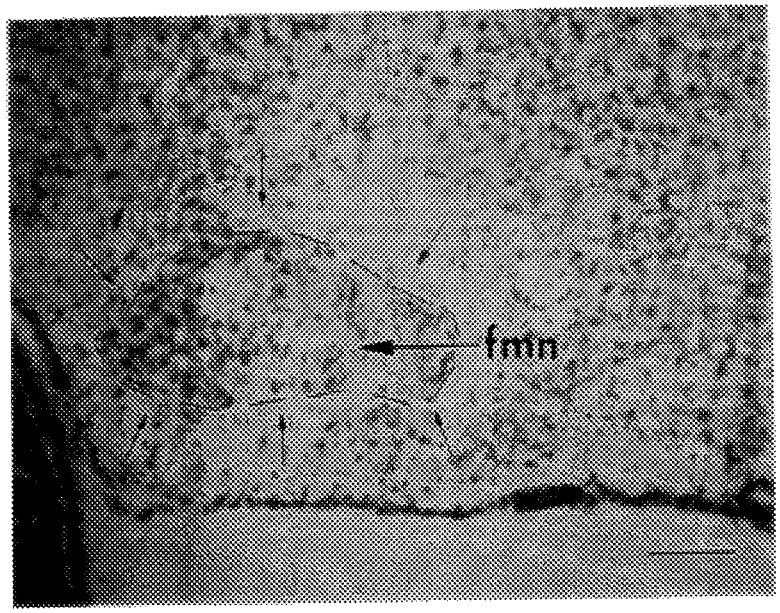
Figure 3D:
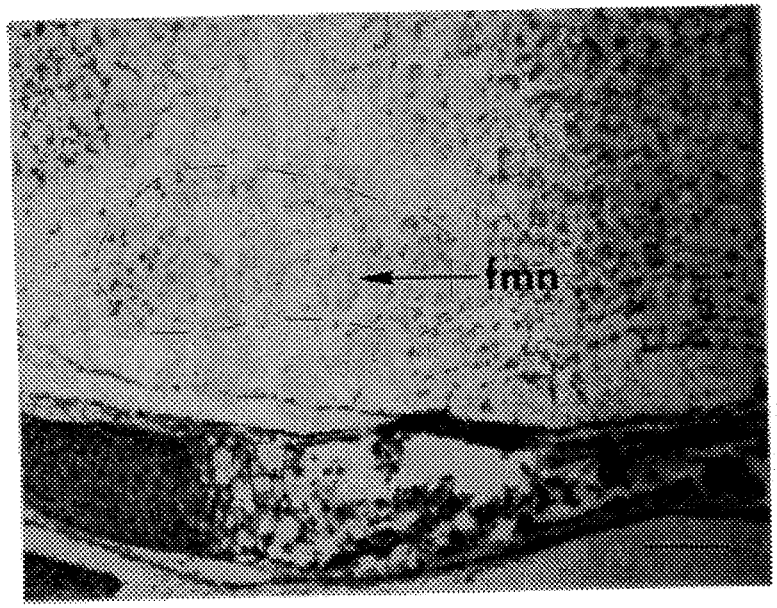
Figure 4B:
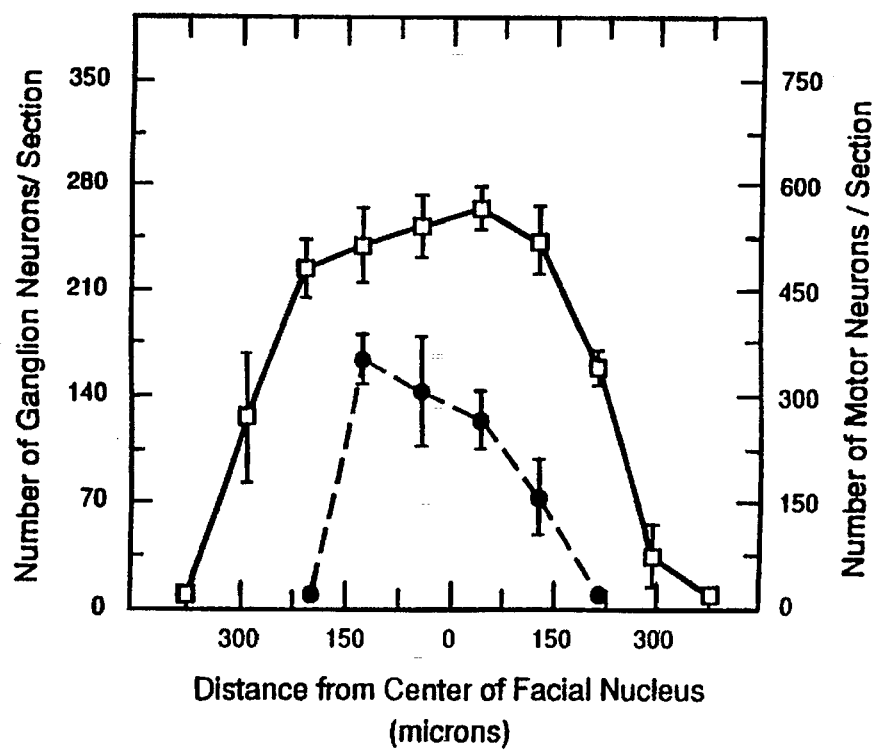

The nucleus of the facial nerve lies as a discrete group of cells in the rostroventral brainstem, which enervates the musculature of the head and neck. This nucleus is characterized by a dense group of large neurons surrounded by a halo of reduced cellular density (FIG. 3C, D). Qualitative comparisons between the trkB$^{TK}$ (−/−) mice with the corresponding (+/+) and (±) animals showed that the wild-type facial nucleus had a greater density than that of the (−/−) mutant mice (FIG. 4B). Subsequent counts of facial motor neurons in the trkB$^{TK}$ (+/+) and (−/−) mice showed a significant difference between the two groups. Whereas the trkB$^{TK}$ (+/+) mice had 3,291±357 neurons (n=4), the (−/−) mice only had 1,019±65 (n=4) (p<0.002). These cellular deficiencies encompass each of the nuclei's subdivisions. The number of motor neurons in the (+/+) mice correspond to those reported by Herrup et al., (1984).

Other Neuronal Deficiencies in trkB$^{TK}$ (−/−) mice

Figure 5A:
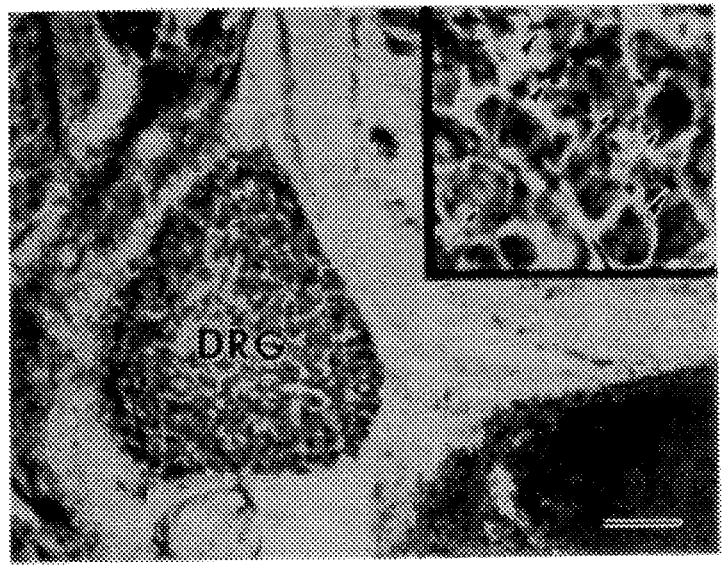

BDNF, a cognate ligand for the trkB receptors, can support the growth and survival of neurons from DRG in vitro (Lindsay et al., 1985; Kalcheim et al., 1987). To examine whether the trkB$^{TK}$ (−/−) mice had any additional neuronal defects in these structures as a consequence of loss of gp145$^{trkB}$ expression, we counted DRG cells from the T11 to the L3 region of the spinal cord. As illustrated in FIG. 5A, we observed an approximately 50% decrease in the number of cells in the DRG. The DRG cells counted from the trkB$^{TK}$ (±) animals segregated with the (+/+) wild type mice. The loss in cell number in these ganglia is also apparent by their significantly reduced size in the trkB$^{TK}$ (−/−) mice (FIG. 3E, F).

Figure 5B:
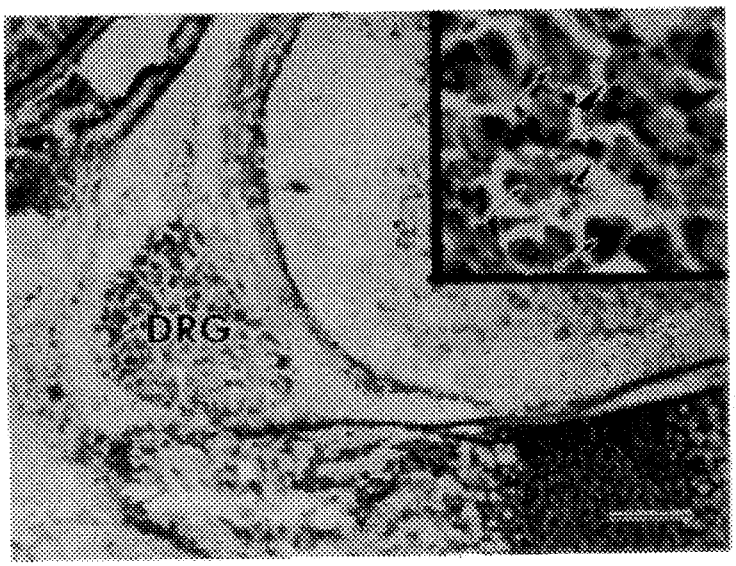
Figure 5C:
Figure 5D:
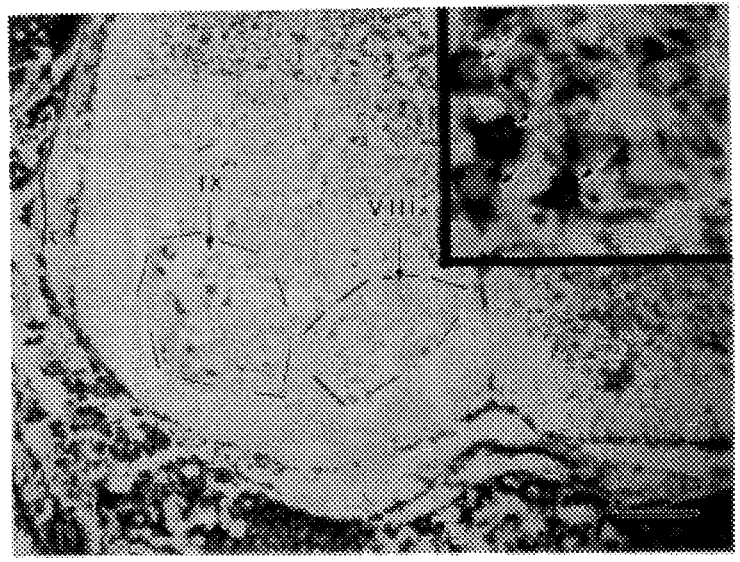

Recent studies have indicated that BDNF can prevent cell death of axotomixed motor neurons in newborn rats (Sendtner et al., 1992; Yan et al., 1992). Moreover, BDN F has also been shown to prevent naturally occurring and differentiation-induced cell death of lumbosacral motor neurons in chick embryos (Oppenheim et al., 1992). Therefore, we examined the number of lumbar motor neurons in the spinal cord of trkB$^{TK}$ (+/+) and (−/−) mice (FIG. 3 G,H). The number of motor neurons from the (+/+) animals were significantly (p<0.01) higher (2,552±97; n=4) than that counted in the trkB$^{TK}$ (−/−) mice (1,667±72; n=4), particularly in those neurons located in spinal cord levels L2 to L5 (FIG. 5B). No differences were observed in the sacral S1 region (FIG. 5B). The number of motor neurons present in the trkB$^{TK}$ (±) mice were not statistically different from those counted in the (+/+) animals. Despite the cell loss seen in the trkB$^{TK}$ (−/−) animals, the remaining lumbar motor neurons appear identical to those of their wild type litter mates (FIG. 3G, H).

trkB transcripts have been described in a variety of other neural structures including the cerebral cortex, the pyramidal cell layer of the hippocampus, thalamus and Purkinje cells (Klein et al., 1989; 1990a, b). Qualitative microscopic examination of these regions did not reveal any detectable changes in the trkB$^{TK}$ (−/−) mice when compared to their normal (+/+) or (±) litter mates.

Discussion

The preferred embodiment concerns transgenic mice lacking a functional gp145$^{trkB}$ tyrosine protein kinase receptor by specifically targeting those trkB sequences encoding its catalytic kinase domain. This defect is likely to disrupt trophic signaling by its two primary ligands BDNF (Klein eta., 1991b; Soppet et al., 1991; Squinto et al., 1991) and NT-4 (Berkemeier et al., 1991, Klein et., 1992; Ip et al., 1992). gp145$^{trkB}$ can also serve as a receptor for the related NT-3 (Glass etal., 1991; Klein et al., 1991b) but only when ectopically expressed in non-neuronal cells (Ip etal., 1993). Therefore, it is unlikely that disruption of gp145$^{trkB}$ expression in the trkB$^{TK}$ (−/−) mice has a significant effect on NT-3 signaling in vivo.

The trkB locus encodes a second class of neurotrophin receptors lacking the kinase catalytic domain (Klein et al., 1990a; Middlemas et al., 1991). At least one of these receptors, gp95$^{trkB}$, is expressed at high levels in the adult mouse brain, particularly in the ependymal layer of certain cranial ventricles and in the choroid plexus (Klein et al., 1990a). Our targeting strategy was aimed at avoiding disruption of this receptor. Indeed, Western blot analysis of brain extracts obtained from P0 trkB$^{TK}$ (−/−) mice revealed that whereas gp145$^{trkB}$ is undetectable, gp95$^{trkB}$ is expressed at levels comparable to those of the (+/+) and (±) mice. Therefore the phenotypic abnormalities observed in the targeted trkB$^{TK}$ (−/−) mice are likely to be due to the specific disruption of signaling through the gp145$^{trkB}$ tyrosine protein kinase receptor.

At birth, the trkB$^{TK}$ (−/−) mice appear morphologically indistinguishable from their (+/+) and (±) siblings. However, the (−/−) mice do not show any signs of feeding activity as determined by the absence of milk in their stomachs. At P1, the trkB$^{TK}$ (−/−) mice are already smaller in size and many die. At P2, occasional survivors depict clear signs of cachexia. So far, none of the trkB$^{TK}$ (−/−) mice has survived beyond P3. The inability of these targeted mice to feed is likely to be a consequence, at least in part, of the significant reduction of cells in the trigeminal and facial nuclear systems (Chusid, 1973). These neuronal deficiencies may also account for the observed inability of the trkB$^{TK}$ (−/−) mice to respond to simple external stimuli such as touching their faces or a gentle stroking under their chin. These abnormalities were observed in mice derived from two independent ES cell clones, further indicating that targeting of the trkB locus is directly responsible for these deficiencies.

The trigeminal ganglion of the trkB$^{TK}$ (−/−) mice only contains 40% of neurons present in their (+/+) or (±) siblings. In situ hybridization analysis of mouse embryos has shown an intense and rather homogeneous expression of trkB transcripts in this ganglion at E9.5 (see FIG. 2 in Klein et al., 1990b). However, at E14.5, trkB expression appears spotty and in less than half of the cells (see FIG. 6 in Klein et al., 1989). Neuronal cell loss in the trigeminal ganglion does not appear to be evenly distributed, with most of the missing cells corresponding to those derived from the anterior portions of the ganglion. A possible explanation for this observation comes from embryological studies in chickens, which indicate that the antedor parts of the ganglion are derived from the non-NGF-dependent ectodermal placodes (D'Amico-Martel and Noden, 1983). Although the duality of trigeminal origin has not been conclusively established in mammals, the pattern of cell loss seen in the homozygous trkB$^{TK}$ (−/−) animals appears to conform to the distribution of fibers and cells that contribute primarily to the mandibular and maxillary branches of the mammalian trigeminal nerve (Erzurumlu and Killackey, 1983). In this study, we only examined the peripheral control of sensory function in the facial region of the trkB$^{TK}$ (−/−) mice. We do anticipate however, that CNS regions that subserve the same sensomotor functions may also be affected. This hypothesis is supported by a recent study indicating BDNF dependence of mesencephalic trigeminal neurons (Von Bartheld and Bothwell, 1993).

The efferent limb for feeding behavior is controlled by motor neurons located in the facial nucleus as well as by the motor fibers of the maxillary division of the trigeminal nerve (Walton, 1977). The significant loss of motor neurons in the facial nucleus (up to 70%) observed in the trkB$^{TK}$ (−/−) mice is likely to disable their mastication muscles and therefore cause their apparent inability to suckle. These findings are in agreement with the recent observations of Sendtner et al. (1992) indicating that BDNF, one of the cognate ligands of gp145$^{trkB}$, can prevent death of facial motor neurons after axotomization of the facial nerve in newborn rats. The protective activity of BDNF on facial neurons following axotomy is not restricted to those of the facial nucleus. Recent studies have indicated that this neurotrophin also has survival promoting effects on spinal motor neurons following transection of the sciatic nerve in newborn rats (Yan et al., 1992) and can rescue chick embryonic motor neurons from naturally occurring cell death (Oppenheim et al., 1992). The significance of these observations is underscored by our results with the trkBTK (−/−) mice, which demonstrate that signaling though the gp145$^{trkB}$ receptor, either by BDNF or by NT-4, is an absolute requirement for survival of at least 1/3 of the lumbar spinal motor neurons.

In situ hybridization studies have indicated that trkB is abundantly expressed in the spinal cord throughout embryonic development (Klein et al., 1989; 1990b). Yet, gross examination of spinal cord cells does not reveal dramatic differences between the trkB$^{TK}$ (−/−) and (+/+) mice, other than in the motor neuron population. A similar observation has been made in other parts of the mouse nervous system known to express high levels of trkB transcripts such as the cerebral cortex, the pyramidal cell layer of the hippocampus and the thalamus. It is possible that some deficiencies will be found in these structures after more detailed analysis. However, it is also possible that certain gp145$^{trkB}$ expressing neurons may survive in the absence of this receptor thanks to compensatory mechanisms, perhaps provided by the highly related trkC tyrosine protein kinase receptors. Indeed, trkC transcripts are also abundant in the spinal cord, cerebral cortex and hippocampus (Lamballe et al., 1991 and submitted; Merlio et al., 1992). The recent availability of mice carrying a targeted trkC gene should help to establish the relative contributions of these tyrosine protein kinases to neuronal survival in these structures.

Interestingly, one of the structures showing obvious deficiencies in the trkB$^{TK}$ (−/−) mice are the DRGs, which are known to express transcripts from each of the three known members of the trk gene family, trk, trkB and trkC (Martin-Zanca et al., 1990; Klein et al., 1990b; Ernfors et al., 1992; Lamballe et al., submitted). Yet in this study, about 50% of their neurons are absent and their overall size is considerably smaller. A possible explanation for the observed cell loss is that each of the members of the trk gene family has a distinct function and do not complement each other. Alternatively, each of these genes might be individually expressed in specific subsets of neurons rendering them responsive to specific members of the NGF neurotrophin family. In support of this hypothesis, DiStefano et al., (1992) have observed that radiolabeled NGF, BDNF and NT-3 recognize different neuronal subpopulations in adult DRGs. Moreover, cultivation of E14 rat DRG neurons in the presence of either NGF, BDNF or NT-3 results in the survival of cells specifically expressing trk, trkB or trkC mRNAs, respectively (Ip et al., 1993). These observations suggest that only a very limited number of DRG neurons, if any, express more than one member of the trk gene family of receptors. If so, the observed cell loss in these ganglia is likely to correspond to that subset of neurons that only express gp145$^{trkB}$.

Regardless of the significant abnormalities observed in the DRGs of trkB$^{TK}$ (−/−) mice, it is unlikely that they contribute to their demise, since none of these mice have survived beyond P3. Additional studies will be necessary to evaluate the full extent of neuronai deficiencies caused by the disruption of gp145$^{trkB}$ expression, since many defects may not display obvious phenotypic deficiencies in such young animals. Of particular interest will be the analysis of the developing substantia nigra, a structure in which the protective effects of BDNF to chemical insults have been already illustrated (Hyman et al., 1991; Altar et al., 1992).

The neuronal cell loss observed in the trkB$^{TK}$ (−/−) animals might be due either to abnormal developmental differentiation or inadequate survival. One method to discriminate between these two possibilities is to examine each of the structures known to have neuronal defects in the trkB$^{TK}$ (−/−) animals after neurogenesis, during the period of axon ingrowth or naturally occurring cell death. Two regions where we observed cell loss in the trkB$^{TK}$ (−/−) animals have been analyzed at this critical period of development. They include the trigeminal ganglion at E12 and the motor neurons of the spinal cord at P0. In each case, we found many more pyknotic and fragmented nuclei in the trkB$^{TK}$ (−/−) mice than in their (+/+) or (±) siblings. These observations suggest that a major component of the neuronal cell loss seen in the trkB$^{TK}$ (−/−) mice is due to increased cell death. These findings am in agreement with the studies of Vogel and Davies (1991)indicating that the onset of BDNF dependence might be coordinated with target enervation. It is not known at this time if additional defects during neuronal differentiation may also contribute to the observed phenotype in these trkB$^{TK}$ (−/−) mutant mice.

It has been proposed that trophic signaling through the gp145$^{trkB}$ kinase receptors requires the presence of the low affinity neurotrophin receptor, p75$^{LNGFR}$ (Bothwell, 1991). Support for this hypothesis came from the studies of Hempstead et al., (1991) who reported that the related trk receptors required co-expression of p75$^{LNGFR}$ in order to generate high affinity NGF binding sites. The results of Soppet et al., (1991) indicating that gp145$^{trkB}$ receptors alone also bound BDNF with low affinity in the nanomolar range, provided further support for this hypothesis. Other studies however, have shown that gp145$^{trkB}$ receptors could mediate BDNF and NT-4 signaling in the absence of p75$^{LNGFR}$, albeit in non-neuronal cells (Glass et al., 1991; Ip et al., 1992, 1993; Klein et al., 1991b, 1992; Squinto eta., 1991). More recently, Marsh et al., (1993) have illustrated that gp145$^{trkB}$ can also signal in cultures of hippocampal neurons which do not express p75$^{LNGFR}$ receptors.

Now, genetic studies strongly argue against the gp145$^{trkB}$/p75$^{LNGFR}$ heterodimer receptor model (Bothwell, 1991). Unlike the trkB$^{TK}$ (−/−) animals described in this study, homozygous (−/−) mice carrying a targeted p75$^{LNGFR}$ gene develop normally and only display obvious neuronal defects in the sensory enervations of the footpad skin (Lee et al., 1992). Indeed, since p75$^{LNGFR}$ serves as a receptor for each of the four known members of the NGF neurotrophin family (Rodriguez-Tebar et al., 1990, 1992; Hallböok et al., 1991), the gp145$^{trkB}$/p75$^{LNGFR}$ heterodimer model predicts that the absence of p75$^{LNGFR}$ would result in a more severe phenotype than mutations in any of the individual members of the trk gene family of kinase receptors. Our findings however, do not rule out the possibility that p75$^{LNGFR}$ may play an auxiliary role in gp145$^{trkB}$ signaling. Crossing the trkB$^{TK}$ (±) and p75$^{LNGFR}$ (±) mice should provide valuable information regarding the contributions of these two classes of neurotrophin receptors to the development and maintenance of the mammalian nervous system.

The invention will now be further described by the following working examples, which are preferred embodiments of the invention. These examples are illustrative rather than limiting. Unless otherwise indicated, all temperatures are in degrees Celsius (° C.). Although the following specific examples all concern TrkB, those having ordinary skill in the art would be able to adapt these procedures to other members of the trk family of receptors.

EXAMPLE 1

Targeting vector

The targeting vector, pFRK90, consisted of 8.1 kbp of trkB genomic sequences (850 bp in the short arm and 7.25 kbp in the long arm), a phosphoglycerate kinase-1 (PG K-1)/neo cassette inserted within trkB coding sequences and a flanking HSV thymidine kinase (tk) cassette (FIG. 1). To generate pFRK90, we first screened an NIH3T3 mouse genomic library with a 2.7 kbp SalI cDNA fragment of pFRK43 (Klein et al., 1989) encompassing those sequences encoding the transmembrane and cytoplasmic domains of gp145$^{TrkB}$. One of the recombinant phages (#12) contained a 21 kbp long insert which included the second (K2) and third (K3) exons of the trkB tyrosine protein kinase region. A 4.8 kbp HindIII DNA fragment was used to generate the short arm of pFRK90 by PCR-aided amplification using as amplimers a 5' primer (SEQ. ID. NO.: 1) having the sequence 5'-CCTTGGGGGGGGTCTTCAGAATTTAT-TAAAGAG-3' which annealed to intron sequences 750 bp upstream of exon K2, and a 3' primer (SEQ. ID. NO.: 2)

5'-GTCGCCCTCGAGACAGACACADTAGAACTTG-3') that annealed to exon K2 sequences (nucleotides 2311 to 2341 of pFRK43). The underlined sequences correspond to NotI (5' primer) and XhoI (3' primer) cleavage sites used for subcloning purposes. This 850 bp NotI-XhoI PCR-amplified DNA fragment was subcloned into pBluescript along with a 1.9 kbp XhoI-SalI PGK-1/neo cassette derived from pKJ-1 (McBurney et al., 1991). The resulting 2.75 kbp NotI-SalI DNA fragment was subsequently ligated to a 3.85 kbp SalI-ClaI DNA fragment containing the 3'35 bp of exon K2 followed by 3.8 kbp of downstream intronic sequences. The SalI cleavage site of this 3.85 kbp SalI-ClaI DNA fragment was engineered by PCR-aided amplification of exon K2 sequences in a manner that eliminated 33 bp (nucleotides 2330 to 2362 of pFRK43) from exon K2. The 6.6 kbp NotI-ClaI trkB DNA fragment containing the PGK-1/neo cassette inserted within exon K2 sequences was next subcloned into the NotI-ClaI sites of pFRK75, a pGEM-9Zf(−)-derived vector containing the HSV tk cassette of pMC1TKpA (Mansour et al., 1988). The resulting plasmid, pLL41, was utilized to generate the targeting vector pFRK90 by adding an additional 3.4 kbp ClaI genomic DNA fragment of phage #12, corresponding to those sequences immediately downstream from the 3.85 kbp SalI-ClaI DNA fragment, thus increasing to 7.25 kbp the total length of the long arm of pFRK90.

Transfection of ES cells and Blastocyst Injection

Cell culture and electroporation of male D3 ES cells (Doetschman et al., 1987) were essentially done as described (Wurst and Joyner, in press). ES cells were trypsinized, washed in PBS and electroplated with 40 pg of NotI-linearized pFRK90 per 5×10$^6$ cells using a Bio-Rad Gene Pulser (240V, 500 μF). Cells were seeded onto 100-mm gelatinized culture dishes at a density of 2.5×10$^6$ cells per plate in ES cell culture medium containing 15% fetal calf serum and 500 U/mL of LIF. After 48 hours, cells were subjected to double selection with 250 μg/mL of G418 and 2.2 μM gancyclovir. Colonies were picked 10 days after transfection using the half colony method as described (Joyner et al., 1989). Positive cell clones (see below) were picked and transferred onto a monolayer of mitomycin C-treated mouse embryonic feeder cells in ES cell medium without G418 or LIF. For blastocyst injections, cells were trypsinized, washed in PBS, and kept on ice. Approximately 15 cells were injected into C57Bl/6 blastocysts as described (Joyner et al., 1989) which were then transferred into the uterus of pseudopregnant CD1 females. The resulting chimeras were bred onto a C57Bl/6J background.

PCR Screening and Southern blot analysis

Pools of 20 individual G41 8$^R$/Ganc$^R$ ES transformants were tested for homologous recombination with pFRK90 DNA as described (Joyner et al., 1989). Briefly, approximately 10$^4$ cells were lysed by freezing and thawing in deionized water and treated with Proteinase K for 2 hours at 50° C. Half the sample was submitted to PCR amplification [94° C. (1 minute), 65° C. (2 minutes) and 72° C. (3 minutes) for 40 cycles] in the presence of 1.25 mM MgCl$_2$ and 10 mM. NTPs. The 5' amplimer (SEQ. ID. NO.: 3), having the sequence

5'-GCTGGACACTGGGACTGCCAGGCC-3' corresponded to genomic sequences located 20 bp upstream of the 5' end of the short arm of pFRK90. The 3' amplimer (SEQ. ID. NO.: 4) having the sequence 5'-CTACCCGGTAGGTAGAATTCCTCGAG-3' contained the EcoRI and KhoI cleavage sites (underlined) located at the junction between the exon K2 sequences and the PGK-1/neo cassette and 10 bp from the PGK-1 promoter (nucleotides -518 to -507; see Adra et al., 1987) (FIG. 1A). One fifth of the PCR-amplified samples was analyzed by electrophoresis through a 1.5% agarose gel. Gels were soaked for 30 minutes in denaturing solution (0.5M NaOH, 1.5M NaCl), the DNA fragments blotted for 90 minutes onto Genescreen membranes (Dupont). Blotted DNA was cross-linked to the membrane by UV light and hybridized in hybridization buffer [0.5M sodium phosphate, pH 7.0, 7% SDS, 15% formamide, 1 mM EDTA, and 10 mg/mL BSA] for 3 hours at 60° C. to a [$^{32}$P]-labeled 850-bp DNA probe derived by PCR amplification of the short arm of pFRK90. The hybridized membrane was washed twice for 30 minutes with 150 m.M sodium phosphate buffer, pH 7.0, containing 0.1% SDS, once for 30 minutes with 30 mM sodium phosphate buffer pH 7.0, 0.1% SDS, air dried and exposed to Kodak X-Omat film at –70° C. with the help of an intensifying screen. For Southern analysis of genomic DNA, ES cells were grown to confluence in 24-well plates and the DNA was extracted as described (Laird et al., 1991). DNA (10 µg) was digested with BamHI or KpnI, electrophoresed on a 0.7% agarose gel, blotted and hybridized as described above with a [$^{32}$P], labeled 1.4 kbp XhoI-HindIII DNA fragment derived from phage #12 genomic sequences located immediately upstream of the 5' end of the targeting vector pFRK90 (FIG. 1A).

Immunoblotting

Western blot analysis of trkB proteins was essentially performed as described (Klein et al., 1990a). Briefly, newborn heads or brains were homogenized (0.1 g/mL) in immunoprecipitation buffer containing 2.5 U/mL aprotinin and 1 mM PMSF and the resulting extracts clarified by centrifugation. The catalytic gp145$^{trkB}$ receptors were immunoprecipitated with a trkB mouse monoclonal antibody 18-29.2 (unpublished results), followed by incubation with a secondary rabbit anti-mouse IgG antiserum and protein A - Sepharose. The non-catalytic gp95$^{trkB}$ receptor was immunoprecipitated by incubation with a rabbit polyclonal antiserum (#104) raised against a peptide corresponding to the 13 carboxy-terminal residues of gp95$^{trkB}$ (Klein et al., 1990a). Immunoprecipitates were separated by 7.5% SDS-PAGE, blotted onto nitrocellulose filters and incubated with either a cross-reactive rabbit polyclonal antiserum raised against a peptide corresponding to the 14 carboxy-terminal amino acid residues of gp140I$^{trk}$ (Santa Cruz Biotech., Inc.) to identify gp145$^{trkB}$ or antiserum #104 to identify gp95$^{trkB}$. Immunoblots were incubated with [$^{125}$I]-labeled protein A (5.6 µCi/µg, 5 µCi per 10 mL of Tris-buffered saline) and exposed to Kodak X-Omat film at –70° C. for the required length of time in the presence of intensifying screens.

Histology and Morphometric Analysis

Newborn mice (P0) from a heterozygous trkB/TK (±) mating pair were transcardially perfused with 4% paraformaide hyde in PBS, decapitated, and the heads and bodies placed into fresh fixative for 2 to 4 hours. Following this short post-fixation, tissues were cryoprotected in 30% sucrose/PBS overnight at 4° C. For sectioning, heads were blocked in the coronal plane and embedded in tissue freezing medium H-TFM (Triangle Biomedical Sciences) at –58° C. After allowing the block to warm to –26° C., serial frozen sections were taken at 15 µm, thaw-mounted onto Superfrost-Plus slides (Fisher), allowed to air-dry, and stained with cresyl violet acetate. The trigeminal ganglion and brainstem FMN were identified and their anterior-to-posterior limits mapped. The facial motor neurons and trigeminal ganglion cells were identified by their large size and distinct nucleus. Cells were counted at 400X in all focal planes at 75 µm intervals by two people. In all cases, variability in cell counts between the two counters was less than 5%. Areas of the two nuclei were determined using a morphometric program (SigmaScan, Jandel) attached to a digitizing tablet and drawing tube. For counts of DRG neurons and motor neurons, whole P0 bodies were mounted in the coronal plane and sedal sections were collected and stained as above. Spinal levels were determined by a combination of mapping the beginning and end of each individual vertebrae and DRG as well as through characteristic changes in spinal cord shape. Counts of DRG neurons were taken from ganglia at spinal cord levels T11-L3. Caudal limits of the lumbar cord (L5/S 1) were identified by a dramatic decrease in the number of motor neurons as well as a reduction in size of the ventral horn. Motor neurons in the ventral horn of the spinal cord (laminae 8 and 9) were identified by their dark staining cytoplasm and pale nucleus. Only those neurons that had a visible nucleus were counted. Raw cell counts were adjusted for split nuclei using the Abercrombie (1946) correction factor.

Abbreviations

The abbreviations used throughout this specification have the following meanings, unless otherwise indicated in specific instances.

| | |
|---|---|
| bp | base pairs |
| BDNF | brain-derived neurotrophic factor |
| BSA | bovine serum albumin |
| CNS | central nervous system |
| DNA | deoxyribonucleic acid |
| DRG | dorsal root ganglion |
| EDTA | ethylenediaminetetraacetic acid |
| ES | embryonic stem |
| FMN | facial motor nucleus |
| HSV | herpes simplex virus |
| kbp | kilo base pairs |
| LIF | leukocyte inhibitory factor |
| NGF | nerve growth factor |
| NT | neurotrophin |
| NTP | nucleotide triphosphates |
| PAGE | polyacrylamide gel electrophoresis |
| PBS | phosphate-buffered saline |
| PCR | polymerase chain reaction |
| PNS | peripheral nervous system |
| SDS | sodium dodecyl sulfate |
| SEM | — |
| TK | tyrosine kinase |

| Abbreviations |  |
|---|---|
| The abbreviations used throughout this specification have the following meanings, unless otherwise indicated in specific instances. | |
| UV | ultraviolet |

References

Abercrombie, M. (1946) Estimation of nuclear populations from microtome sections. *Anatomical Record* 94, 239–247.

Adra, C. N., Boer, P. H., and McBurney, M. W. (1987). Cloning and expression of the mouse pgk-1 gene and the nucleotide sequence of its promoter. *Gene* 60, 65–74.

Altar, C. A., Boylan, C. B., Jackson, C., Hershenson, S., Miller, J., Wiegand, S. J., Lindsay, R. M., and Hyman, C. (1992). Brain-derived neurotrophic factor augments rotational behavior and nigrostriatal dopamine turnover in vivo. *Proc. Natl. Acad. Sci USA* 89, 11347–11351.

Barbacid, M. (1993). Nerve Growth Factor: A tale of two receptors. *Oncogene*, in press.

Berkemeier, L. R., Winslow J. W., Kaplan, D. R., Nikolics, K., Goeddel, D. V., and Rosenthal, A. (1991). Neurotrophin-5: A novel neurotrophic factor that activates trk and trkB. *NeuronI* 7, 857–866.

Bothwell, M. (1991). Keeping track of neurotrophin receptors. *Cell* 65, 915–91 8.

Chao, M. V. (1992). Neurotrophin receptors: a window into neuronal differentiation. *Neuron* 9, 583–593.

Chusid, J. G. Correlative Neuroanatomy and Functional Neurology. Los Altos: Lange Medical Publishing. 1973

D'Amico-Martel, A. and Noden, D. M. (1983). Contributions of placodal and neural crest cells to evian cranial peripheral ganglia. *American Journal of Anatomy* 166, 445–468.

Davies, A. and Lumsden, A. (1984). Relation of target encounter and neuronal cell death to nerve growth factor responsiveness in the developing mouse trigeminal ganglion. *Journal of Comparative Neurology* 223, 124–137.

DeChiara, T. M., etal., (1990) *Nature* 345, 78.

DiStefano, P. S., Friedman, B., Radziejewski, C., Alexander, C., Boland, P., Schick, C. M., Lindsey, R. M. and Wiegand, S. J. (1992). The neurotrophins BDNF, NT-3 and NGF display distinct patterns of retrograde axonal transport in peripheral and central neurons. *Neuron* 8, 983–993.

Doetschman, T., Gregg, R. G., Maeda, N., Hooper, M. L., Melton, D. W., Thompson, S., and Smithies, O. (1987). Targeted correction of a mutant HPRT gene in mouse embryonic stem cells. *Nature* 330, 576–578.

Ernfors, P., Meriio, J. -P., Persson, H. (1992). Cells expressing mRNA for neurotrophins and their receptors during embryonic rat development. *European Journal of Neuroscience* 4, 1140–1158.

Erzurumlu, R. S., and Killackey, H. P. (1983). Development of order in the rat trigeminal system. *Journal of Comparative Neurology* 213, 365–380.

Glass, D. J., Nye, S. H., Hantzopoulos, P., Macchi, M. J., Squinto, S. P., Goldfarb, M., and Yancopoulos, G. D. (1991). TrkB mediates BDNF/NT-3 dependent survival and proliferation of fibroblasts lacking the low affinity NGF receptor. *Cell* 66, 405–413.

Hallböok, F., Ibanez, C. F., and Persson, H. (1991). Evolutionary studies of the nerve-growth factor family reveal a novel member abundantly expressed in Xenopus ovary. *Neuron* 6, 845–858.

Hanks, S. K., Quinn, A. M., and Hunter, T. (1988). The protein kinase family: conserved features and deduced phylogeny of the catalytic domains. *Science* 241, 42–52.

Hempstead, B. L., Martin-Zanca, D., Kaplan, D. R., Parada, L. F., and Chao, M. W. (1991). High-affinity NGF binding requires coexpression of the trk proto-oncogene and the low-affinity NGF receptor. *Nature* 350, 678–683.

Herrup, K., Diglio, T. J. and Letsou, A. (1984). Cell lineage relationships in the development of the mammalian CNS. I. The facial nerve nucleus. *Dev. Biology.* 103, 329–326.

Hyman, C., Hofer, M., Barde, Y -A., Juhasz, M., Yancopoulos, G. D., Squinto, S. P., and Lindsay, R. M. (1991). BDNF is a neurotrophic factor for dopaminergic neurons of the substantia nigra. *Nature* 350, 230–235.

Ip N. Y., Ibanez, C. F., Nye, S. H., McClain, J., Jones P. F., Gies, D. R., Belluscio, L., LeBeau, M. M., Espinosa III, R., Squinto, S. P., Persson, H., and Yancopoulos, G. D. (1992). Mammalian neurotrophin-4: structure, chromosomal location, tissue distribution, and receptor specificity. *Proc. Natl. Aced. Sci. USA* 89, 3060–3064.

Ip, N. Y., Stitt, T. N., Tapley, P., Klein, R., Glass D. J., Fandl, J., Greene, L. A., Barbacid, M., and Yancopoulos, G. D. (1993). Similarities and differences in the way neurotrophins interact with the Trks in neuronal and non-neuronai cells. *Neuron* 10, 137–149.

Joyner, A. L., Skarnes, W. C., and Rossant, J. (1989). Production of a mutation in mouse En-2 gene by homologous recombination in embryonic stem cells. *Nature* 338, 153–156.

Kalcheim, C., Barde, Y. -A., Thoenen, H. and Le Douarin, N. (1987). In vivo effect of a brain-derived neurotrophic factor on the survival of developing dorsal root ganglion cells. *EMBP J* 6, 2871–2873.

Kaplan, D. R., Martin-Zanca, D., and Parada, L. F. (1991). Tyrosine phosphorylation and tyrosine kinase activity of the trk proto-oncogene product induced by NGF. *Nature* 350, 158–160.

Klein, R., Parade, L. F., Coulier, F., and Barbacid, M. (1989). trkB, a novel tyrosine protein kinase receptor expressed during mouse neural development. *EMBO J.* 8, 3701–3709.

Klein, R., Conway, D., Parade L. F., and Barbacid, M. (1990a). The trkB tyrosine protein kinase gene codes, for a second neurogenic receptor that lacks the catalytic kinase domain. *Cell* 5.1., 647–656.

Klein, R., Martin-Zanca, D., Barbacid, M. and Parada, L. F. (1990b). Expression of the tyrosine kinase receptor gene trkB is confined to the mudne embryonic and adult nervous system. *Development* 109, 845–850.

Klein, R., Jing, S., Nandud, V., O'Rourke, E., and Barbacid, M. (1991a). The trk proto-oncogene encodes a receptor for nerve growth factor. *Cell* 65, 189–197.

Klein, R., Nandud, V., Jing, S., Lamballe, F., Tapley, P., Bryant, S., Cordon-Cardo, C., Jones, K. R., Reichardt, L. F., and Barbacid, M. (1991b). The trkB tyrosine protein kinase is a receptor for brain-derived neurotrophic factor and neurotrophin-3. *Cell* 66, 395–403.

Klein, R., Lamballe, F., Bryant, S., and Barbacid, M. (1992). The trkB tyrosine protein kinase is a receptor for neurotrophin-4. *Neuron* 8, 947–956.

Laird, P. W., Zijderweld, A., Linders, K., Rudnicki, M. A., Jaenisch, R., and Berns, A. (1991). Simplified mammalian DNA isolation procedure. *Nucleic Acids Research* 19, 4293.

Lamballe, F., Klein, R., and Barbacid, M. (1991). trkC, a new member of the trk family of tyrosine protein kinases, is a receptor for neurotrophin-3. *Cell* 66, 967–979.

Lee, K. F., Li, E., Huber, L. J., Landis, S. C., Sharpe, A. H., Chao, M. V., and Jaenisch, R. (1992). Targeted mutation of the gene encoding the low affinity NGF receptor p75 leads to deficits in the peripheral sensory nervous system. *Cell* 69, 737–749.

Lindsey, R. M., Thoenen, H., and Barde, Y. -A. (1985). Placode and neural crest-derived sensory neurons are responsive at early developmental stages to brain-derived neurotrophic factor. *Dev. Biology* 112, 319–328.

Mansour, S. L., Thomas, K. R., and Capecchi, M. R. (1988). Disruption of the proto-oncogene int-2 in mouse embryo-derived stem cells: a general strategy for targeting mutations to non-selectable genes. *Nature* 336, 348–352.

Marsh, H. N., Scholz, W. K., Lamballe, F., Klein, R., Nanduri, V., Barbacid, M., and Palfrey, H. C. (1993). Signal transduction events mediated by the BDNF receptor pgl $45^{trkB}$ in primary hippocampal pyramidal cell culture. *J. Neuroscience*, in press.

Martin-Zanca, D., Oskam, R., Mitra, G., Copeland, T., and Barbacid, M. (1989). Molecular and biochemical characterization of the human trk proto-oncogene. *Mol. Cell Biol.* 9, 24–33.

Martin-Zanca, D., Barbacid, M., and Parada, L. F. (1990). Expression of the trk proto-oncogene is restricted to the sensory cranial and spinal ganglia of neural crest origin in mouse development. *Genes Dev.* 4, 683–694.

McBurney, M. W., Sutherland, L. C., Adra, C. N., Leclair, B., Rudnicki, M. A., and Jardine, K. (1991). The mouse Pgk-1 gene promoter contains an upstream activator sequence. *Nucl. Acids Res*, 20, 5755–5761.

McKnight, S. L. (1980). *Nucl. Acids Res*, 8, 5949.

Meakin, S. O. and Shooter, E. M. (1992). The nerve growth factor family of receptors. *Trends Neurosci.* 15, 323–331.

Merlio, J. -P., Ernfors, P., Jaber, M., and. Persson H. (1992). Molecular cloning of rat trkC and distribution of cells expressing messenger RNAs for members of the trk family in the rat central nervous system. *Neuroscience* 51, 513–532.

Middlemas, D. S., Lindberg, R. A., Hunter, T. (1991). trkB, a neural receptor protein-tyrosine kinase: evidence for a full-length and two truncated receptors. *Mol Cell Biol.* 11, 143–153.

Oppenheim, R. W., Qin-Wei, Y., Prevette, D. and Yan, Q. (1992). Brain-derived neurotrophic factor rescues avian motor neurons from cell death. *Nature* 360, 755–757.

Roddguez-Tebar, A., Dechant, G., and Barde, Y. -A. (1990). Binding brain-derived neurotrophic factor to the nerve growth factor receptor. *Neuron* 4, 487–492.

Rodriguez-Tebar, A., Dechant, G., Gotz, R., and Barde, Y. A. A. (1992). Binding of neurotrophin-3 to its neuronal receptors and interactions with nerve growth factor and brain-derived neumtrophic factor. *EMBO J.* 11, 917–922.

Schwartzberg, P. L., et al., (1989). *Science* 246, 799.

Sendtner, M., Holtmann, B., Kolbeck, R., Thoenen, H. and Barde, Y. -A. (1992). Brain-derived neurotrophic factor prevents the death of motoneurons in newborn rats after nerve section. *Nature* 360, 757–759.

Smithies, O. et al. (1985). *Nature* 317, 230.

Soppet, D., Escandon, E., Maragos, J., Middlemas, D. S., Reid, S. W., Burton, L. E., Stanton, B. R., Kaplan, D. R., Hunter, T., Nikolics, K., and Parada L. F. (1991). The neurotrophic factors brain-derived neurotmphic factor and neurotrophin-3 are ligands for the TrkB tyrosine kinase receptor. *Cell* 65, 895–903.

Squinto, S. P., Stitt, T. N., Aldrich, T. H., Davis, S., Bianco, S. M., Radziejewski, C., Glass, D. J., Masiakowski, P., Firth, M. E., Valenzuela, D. M., DiStefano, P. S., and Yancopoulos, G. D. (1991). trkB encodes a functional receptor for brain-derived neurotrophic factor and neurotrophin-3 but not nerve growth factor. *Cell* 65, 885–893.

Trends in Genetics 5(3), 70–76 (1989)

Vogel, K. S. and Davies, A. M. (1991). The duration of neurotrophic factor independence in early sensory neurons is matched to the time course of target field innervation. *Neuron* 7, 819–830.

Von Bartheld, C. S. and Bothwell, M. (1993). Development of the mesencephalic nucleus of the trigeminal nerve in chick embryos: Target innervation, neumtmphin receptors, and cell death. *J. Como. Neurology* 328, 185–202.

Walton, J. N. *Brain's Diseases of the Nervous System*. Eight Edition. Oxford: Oxford University Press. 1977.

Wurst, W. and Joyner, A. L. Production of targeted embryonic stem cell clones. In *Gene Targeting: A Practical Approach*, (A. L. Joyner, ed.) IRL Press, Oxford, in press.

Yan, Q., Elliott, J. and Snider, W. D. (1992). Brain-derived neurotrophic factor rescues spinal motor neurons from axotomy-induced cell death. *Nature*, 753–755.

---

What is claimed is:

1. A mouse homozygous for a disrupted trkB gene, wherein the trkB gene is disrupted by the insertion of a selectable marker sequence and wherein said mouse exhibits a decrease in the number of neurons which comprise the facial motor nucleus, spinal cord, trigeminal ganglia and dorsal root ganglia.

2. A mammalian cell line, wherein the trkB gene is disrupted by the insertion of a selectable marker sequence.

3. The cell line of claim 2 wherein the cell line is an embryonic stem cell line.

* * * * *